United States Patent
Shaz et al.

(10) Patent No.: US 12,258,582 B2
(45) Date of Patent: Mar. 25, 2025

(54) METHOD OF BLOOD POOLING AND STORAGE

(71) Applicant: New York Blood Center, Inc., New York, NY (US)

(72) Inventors: Beth Shaz, New York, NY (US); Christopher D. Hillyer, New York, NY (US)

(73) Assignee: New York Blood Center, Inc., New York, NY (US)

( * ) Notice: Subject to any disclaimer, the term of this patent is extended or adjusted under 35 U.S.C. 154(b) by 1223 days.

(21) Appl. No.: 16/514,689

(22) Filed: Jul. 17, 2019

(65) Prior Publication Data
US 2019/0338248 A1 Nov. 7, 2019

Related U.S. Application Data

(63) Continuation of application No. 13/483,379, filed on May 30, 2012, now Pat. No. 10,385,317, which is a (Continued)

(51) Int. Cl.
*G01N 33/80* (2006.01)
*A01K 5/01* (2006.01)
(Continued)

(52) U.S. Cl.
CPC .......... *C12N 5/0641* (2013.01); *A01K 5/0114* (2013.01); *A01K 5/02* (2013.01); *A01K 5/0291* (2013.01); *A01N 1/02* (2013.01); *A01N 1/021* (2013.01); *A01N 1/0226* (2013.01); *A61K 35/14* (2013.01); *A61K 35/16* (2013.01);
(Continued)

(58) Field of Classification Search
None
See application file for complete search history.

(56) References Cited

U.S. PATENT DOCUMENTS

| 4,540,573 A | 9/1985 | Neurath et al. |
| 4,789,545 A | 12/1988 | Woods et al. |

(Continued)

FOREIGN PATENT DOCUMENTS

| WO | 1993/025295 | 12/1993 |
| WO | 1996/039026 | 12/1996 |

(Continued)

OTHER PUBLICATIONS

Luce et al, Other Critical Care Disorders and Issues in Care of the Critically Ill, Use of Blood Components in the Intensive Care Unit, 2008, Critical Care Medicine, 1655-1675) (Year: 2008).*

(Continued)

*Primary Examiner* — Sharmila G Landau
*Assistant Examiner* — Stephanie A McNeil
(74) *Attorney, Agent, or Firm* — Fish & Richardson P.C.

(57) ABSTRACT

The disclosure provides methods of making a red blood cell, plasma, and platelet products having a uniform dose and volume. The method comprises pooling a plurality of blood units, leukoreducing the blood and inactivating any pathogen contained therein. Plasma, RBCs, and platelets are then divided into uniform dose and volume units which have an extended shelf life.

15 Claims, 3 Drawing Sheets

Related U.S. Application Data continuation-in-part of application No. PCT/US2011/062460, filed on Nov. 29, 2011, and a continuation-in-part of application No. 13/306,759, filed on Nov. 29, 2011, now Pat. No. 8,512,942.

(60) Provisional application No. 61/649,121, filed on May 18, 2012, provisional application No. 61/417,770, filed on Nov. 29, 2010.

(51) Int. Cl.
| | | |
|---|---|---|
| *A01K 5/02* | (2006.01) | |
| *A01N 1/02* | (2006.01) | |
| *A61K 35/14* | (2015.01) | |
| *A61K 35/16* | (2015.01) | |
| *A61K 35/18* | (2015.01) | |
| *A61K 35/19* | (2015.01) | |
| *A61M 1/02* | (2006.01) | |
| *A61M 1/34* | (2006.01) | |
| *C12N 5/078* | (2010.01) | |

(52) U.S. Cl.
CPC .............. *A61K 35/18* (2013.01); *A61K 35/19* (2013.01); *A61M 1/0272* (2013.01); *A61M 1/342* (2013.01); *A61M 1/3496* (2013.01); *C12N 5/0644* (2013.01); *A61M 2202/0429* (2013.01); *A61M 2202/20* (2013.01)

(56) References Cited

U.S. PATENT DOCUMENTS

| | | | |
|---|---|---|---|
| 5,120,649 | A | 6/1992 | Horowitz et al. |
| 5,232,844 | A | 8/1993 | Horowitz et al. |
| 5,541,294 | A | 7/1996 | Horowitz et al. |
| 5,637,451 | A | 6/1997 | Ben-Hur et al. |
| 5,658,722 | A | 8/1997 | Margolis-Nunno et al. |
| 5,670,060 | A | 9/1997 | Matkovich et al. |
| 5,712,086 | A | 1/1998 | Horowitz et al. |
| 5,981,163 | A | 11/1999 | Horowitz et al. |
| 6,077,659 | A | 6/2000 | Ben-Hur et al. |
| 6,080,322 | A | 6/2000 | Deniega et al. |
| 6,090,599 | A | 7/2000 | Ben-Hur |
| 6,136,586 | A | 10/2000 | Budowsky et al. |
| 6,214,534 | B1 | 4/2001 | Horowitz et al. |
| 6,294,361 | B1 | 9/2001 | Horowitz et al. |
| 6,413,714 | B1 | 7/2002 | Margolis-Nunno et al. |
| 6,447,987 | B1 | 9/2002 | Hess et al. |
| 6,491,819 | B2 * | 12/2002 | Prince ..................... A61M 1/34 210/321.67 |
| 6,548,242 | B2 | 4/2003 | Horowitz et al. |
| 6,730,230 | B2 | 5/2004 | Cook et al. |
| 7,186,231 | B2 | 3/2007 | Takagi et al. |
| 8,512,942 | B2 | 8/2013 | Shaz |
| 8,968,993 | B2 | 3/2015 | Shaz et al. |
| 9,394,518 | B2 | 7/2016 | Shaz et al. |
| 9,982,230 | B2 | 5/2018 | Shaz et al. |
| 10,385,317 | B2 | 8/2019 | Shaz et al. |
| 2002/0192632 | A1 | 12/2002 | Hei et al. |
| 2004/0236263 | A1 | 11/2004 | Van Waeg et al. |
| 2008/0050275 | A1 | 2/2008 | Bischof et al. |
| 2011/0230369 | A1 | 9/2011 | Buffet et al. |
| 2012/0111807 | A1 | 5/2012 | Hilyer et al. |
| 2012/0135391 | A1 | 5/2012 | Shaz et al. |
| 2012/0252001 | A1 | 10/2012 | Shaz |
| 2013/0004937 | A1 | 1/2013 | Yoshida et al. |
| 2016/0298083 | A1 | 10/2016 | Shaz et al. |
| 2018/0245043 | A1 | 8/2018 | Shaz et al. |

FOREIGN PATENT DOCUMENTS

| | | |
|---|---|---|
| WO | 1998/041087 | 9/1998 |
| WO | 1998/046073 | 10/1998 |
| WO | 2000/032542 | 6/2000 |
| WO | 2000/074483 | 12/2000 |
| WO | 2003/049784 | 6/2003 |

OTHER PUBLICATIONS

Fast et al, nactivation of Human White Blood Cells in Red Blood Cell Products Using the Mirasol® System for Whole Blood, 2007, Blood 110(11): 2897 (Year: 2007).*

Beutler et al., The definition of anemia: what is the lower limit of normal of the blood hemoglobin concentration? Blood, 107(5): 1747-1750 (2006).

Cardoso et al., Mini-pool screening by nucleic acid testing for heptatis B virus, heptatis C virus, and HIM preliminary results. vol. 38, No. 10, pp. 905-907 (1998).

Deplaine et al., The sensing of poorly deformable red blood cells by the human spleen can be mimicked in vitro. Blood, vol. 117, No. 8, e88-e95 (2011).

Extended European Search Report mailed on Apr. 1, 2014 for European Application 11845230.9.

Fujihara et al., Prestorage leucofiltration prevents the accumulation of matrix metalloproteinase-9 in red cell concentrates stored in mannitol-adenine-phosphate medium. Vox Sanguinis 89(2): 114-115 (2005).

Gilson et al., A novel mouse model of RBC storage and posttransfusion in vivo survival. Transfusion 49(8): 1546-1553 (2009).

Hod et al., Transfusion of human volunteers with older, stored red blood cells produces extravascular hemolysis and circulating non-transferrin-bound iron. Blood, 118(25): 6675-6682 (2011).

Hod et al., Harmful effects of transfusion of older stored red blood cells: iron and inflammation. Transfusion, 51(4): 881-885 (2011).

Hod et al., Use of mouse models to study the mechanisms and consequences of RBC clearance. Vox Sang, 99(2): 99-111 (2010).

Hod et al., Transfusion of red blood cells after prolonged storage produces harmful effects that mediated by iron and Inflammation. Blood, 115(21): 4284-4292 (2010).

Hendrickson et al., Rapid clearance of transfused murine red blood cells is associated with recipient cytokine storm and enhanaced alloimmunogenicity. Transfusion, 51(11): 2445-2454 (2011).

Hess, J.R., For the biomedical excellence for safer transfusion (Best Collaborative). Scientific problems in the regulation of red blood cell products. Transfusion, epub (2012).

International Search report for International Application No. PCT/US2011/062460 mailed Aug. 30, 2012.

Kor DJ et al., Red blood cell storage lesion. Bos J. Basic Med. Sci. 9(SUPP)S21-S27 (2009).

Prince et al., Evaluation of the effect of betapropiolactone/ultraviolet irradiation (BPL/UV) treatment of source plasma on hepatitis transmission by Factor IX complex in chimpanzees. Journal of the International Society on Thrombosis and Haemostatis, 44(3): 138-142 (1980).

Zhang et al., Cell Couter, Blood. Encyclopedia of Medical Devices and Instrumentation, Second Edition, p. 81-90 (2006).

Zimmerman et al., Influence of late irradiation on the in vitro RBC storage variables of leucoreduced RBCs in SAGM additive solution. Vox Sanguinis 100(3): 279-284 (2010).

Zimmerman et al., Influence of prestorage leudoreduction and subsequent irradiation on in vitro red blood cell (RBC) storage variables of RBCs in additive solution saline-adenine-glucose-mannitol. Transfusion 49(1): 75-80 (2009).

Areal et al., Evaluation of Trima Caccel 6.0 systems in routine use. Vox Sanguinis, 99 (Suppl. 1) 174-175 (2010).

Lagerberg et al., Evaluation of the quality of blood components obtained after automated separation of whole body by a new multiunit processor. Transfusion, 53(8):1798-1807 (2013).

Webster J, Cell counter, Blood. Enclyclopedia of medical devices and instrumentation, Second Ed., vol. 2, pp. 31-90 (2006).

Wright-Kanuth et al., Developments in component therapy. Clinical Laboratory Sciences, 15(2):116-124 (2002).

* cited by examiner

METHOD OF BLOOD POOLING AND STORAGE

CROSS-REFERENCE TO RELATED APPLICATIONS

The present application is a continuation of U.S. application Ser. No. 13/483,379, filed May 30, 2012, now U.S. Pat. No. 10,385,317, which claims the benefit under 35 U.S.C. § 119 (e) to U.S. Provisional Application 61/649,121 filed May 18, 2012 and is a continuation-in-part of U.S. application Ser. No. 13/306,759, now U.S. Pat. No. 8,512,942, and International Patent Application PCT/US2011/62460, both filed Nov. 29, 2011, both of which claim the benefit under 35 U.S.C. § 119 (e) to U.S. Provisional Application 61/417,770 filed Nov. 29, 2010, the entire contents of all of which are incorporated by reference herein.

BACKGROUND

A single donation of whole blood can supply red blood cell (RBCs), platelets, and plasma products, which can potentially benefit three different patients. However, blood processing by blood banks is not optimized for quality and reproducibility of blood components. Stored RBCs suffer certain disadvantages. The lifespan of stored RBCs is 42 days, which given the fluctuation of supply and demand for RBCs, can lead to dangerous shortages in times of unexpected need. RBCs can also harbor pathogens that can endanger the recipient if the pathogen is transmitted via transfusion.

In addition, each individual unit of blood collected is fractionated (separated into its components: RBCs, platelets, plasma) resulting in a great degree of variance in the amount of RBCs stored in each unit based on the individual donor characteristics. As a result, the concentration and volume of RBCs varies from unit to unit and thus the number of RBCs administered to a given recipient is variable.

Accordingly, a pathogen-free RBC, platelet or plasma product that has an increased lifespan and provides a uniform dose per unit would be highly desirable.

BRIEF SUMMARY

Disclosed herein are methods of producing uniform dose and volume pathogen-free blood components. Specifically, a method is disclosed for preparing uniform dose blood components from a plurality of whole blood units of the same blood group and type comprising leukoreducing whole blood units to form a leukoreduced blood component, wherein the leukoreduced blood component comprises RBCs, platelets, and plasma; pooling the leukoreduced blood component from the plurality of whole blood units; treating the blood component to inactivate one or more pathogens; removing any inactivating agent, if necessary; separating an RBC component, a platelet component, and a plasma component from the blood component; optionally passing RBCs through a filter to remove poorly-deformable RBCs; adding a storage solution to the RBC component and dividing the RBC into uniform dose and volume units; adding a storage solution to the platelet component and dividing the platelets into uniform dose and volume units; and dividing the plasma component into uniform dose and volume units.

In another embodiment, a method is provided preparing uniform dose blood components from a plurality of whole blood units of the same blood group and type comprising: separating a cellular component and a plasma component from the plurality of whole blood units, wherein the cellular component comprises RBCs, platelets, and white blood cells; pooling the cellular component from the plurality of blood units and pooling the plasma component from the plurality of blood units; treating the plasma component with a solvent/detergent process to inactivate viruses and dividing the plasma into uniform dose and volume units; leukoreducing the cellular component; treating the leukoreduced cellular component to inactivate one or more pathogens; separating the leukoreduced cellular component into an RBC component and a platelet component; optionally passing the RBC component through a filter to remove poorly-deformable RBCs; adding a storage solution to the RBC component and dividing the RBCs into uniform dose and volume units; and adding a storage solution to the platelet component and dividing the platelets into uniform dose and volume units.

In one embodiment, the storage solution comprises at least one material selected from the group consisting of adenine, glucose, phosphate, mannitol, guanosine, and a combination thereof.

In another embodiment, the treating step inactivates one or more pathogens without damaging the structure or function of the non-WBC cell component. Pathogen inactivation may additionally damage WBCs to render them unable to replicate. The one or more pathogens are selected from the group consisting of viruses, bacteria, fungi, prions, parasites, and combinations thereof. In another embodiment, the one or more pathogens are inactivated by at least one method selected from the group consisting of irradiation, and agent that inactivates pathogen DNA/RNA, solvent and detergent, magnetophoresis, immunomagnetic bead technology, filtration, and a combination thereof.

In another embodiment, the method further comprises a step for inactivating residual white blood cells in the pooled blood, RBC or platelet components.

In another embodiment, each unit of the RBC component contains about $1 \times 10^{12}$ to about $5 \times 10^{12}$ RBCs/unit. In another embodiment, each unit of the RBC component contains about 20-80 g of hemoglobin.

In another embodiment, the method further comprises the step of removing poorly-deformable RBCs from the RBC component.

DETAILED DESCRIPTION

Figure 1:
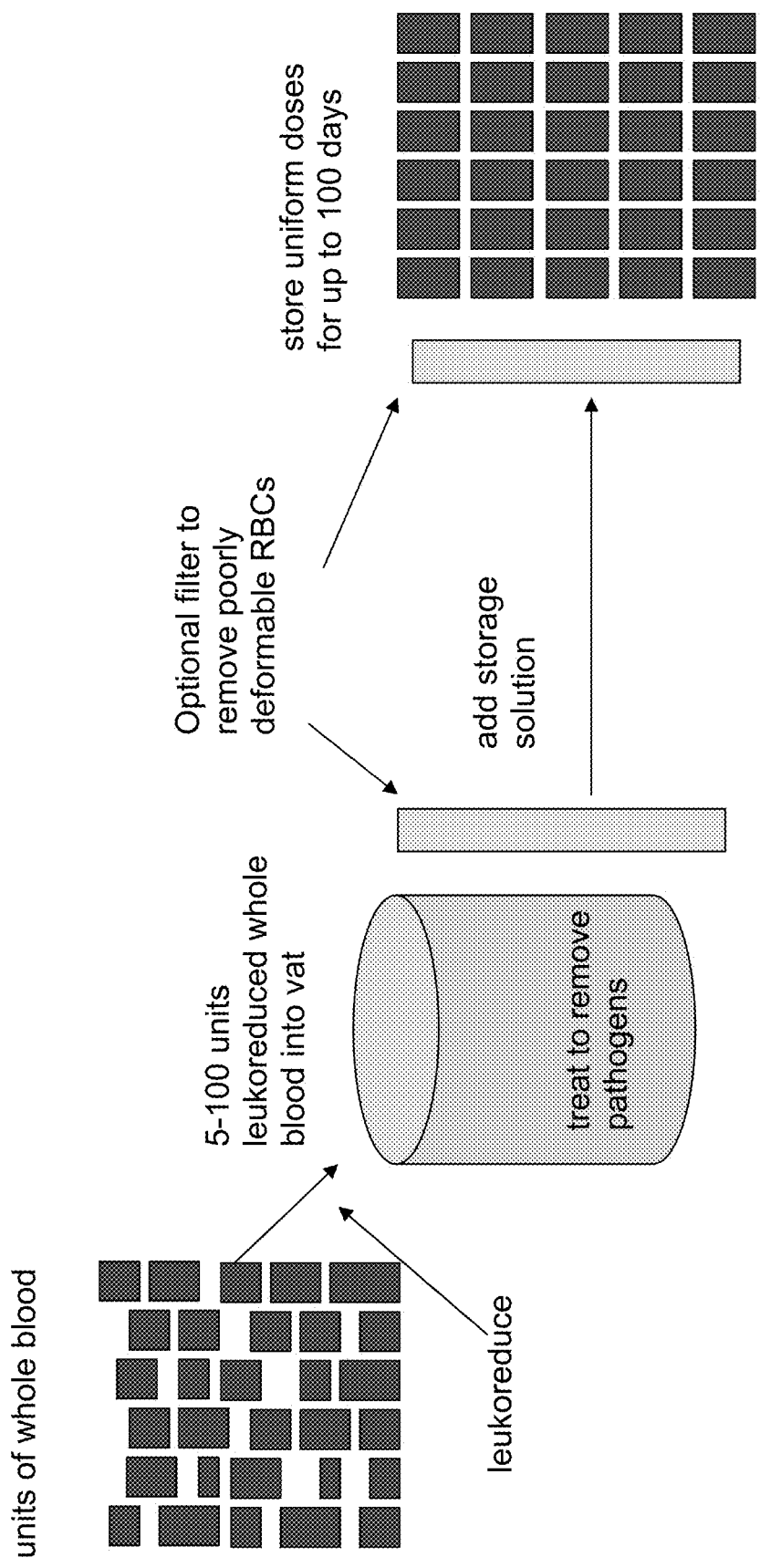
FIG. 1 is a schematic of the steps of a blood pooling, pathogen inactivation, and blood storage method in accordance with an embodiment of the disclosure.

The disclosure provides a method for obtaining a pathogen-free pharmaceutical grade red blood cell (RBC), platelet, or plasma product that contains a uniform unit dose and volume, presents a reduced risk of inducing adverse effects in the recipient, and may have an increased storage life. A further advantage of administering the units obtained according to the disclose methods is the mitigation of adverse events such as transfusion associated graft vs. host disease, disease transmission, transfusion related immunomodulation (potentially resulting in nosocomial infection, multiorgan failure), allergic reactions, febrile nonhemolytic reactions, and transfusion associated lung injury.

In one embodiment, a method of making a cell-containing component is provided that comprises a) obtaining a plurality of whole blood units, b) separating a desired cell component from the blood units, c) leukoreducing the whole blood or the desired cell component, d) pooling the desired cell components from the blood units, e) treating the cell component to inactivate one or more pathogens, and f) adding a storage solution to the cell component. In certain embodiments, the step of inactivating one or more pathogens can take place prior to separating the desired cell component from the pooled blood.

Blood units are obtained from donors according to methods known to persons of ordinary skill in the art. In each embodiment, the blood is segregated according to one or more blood types and/or groups prior to pooling. In certain embodiments, the pooled RBCs or blood units have the same blood type of at least one blood group (ABO, Kell, Duffy, Lewis, MNS, etc.) and type (Rh). The blood units can be typed for one, two or more blood groups and pooled based on the one, two or more blood groups and/or types. In certain embodiments, the pooled blood units each have the same ABO blood group and the same Rh blood type (selected from the group consisting of E, D, C, K, Fya, Fyb, Jka, Jkb, S, e, and c). In another embodiment, the pooled blood units each have the same ABO group but differ in Rh blood type. The donors are typically mammals, such as humans. The donors can be any gender, age, race or ethnicity so long as they are eligible to donate according to US Food and Drug Administration and other accreditation agency criteria. In another embodiment, RBCs are obtained from whole blood or from apheresis donors.

In one embodiment, the obtained blood units are first fractionated and blood components are obtained. The fractionated components are pooled; for example, RBCs from a plurality of blood units are collected and stored together for further processing and subsequent transfusion.

In certain embodiments, the blood cell product is a homogenous RBC product that is obtained by fractionation or other known separation means. Blood and erythrocyte fractionation relies on the unique structure of the RBCs to separate them from plasma and other elements in the blood. Fractionation of whole blood into its constituents is an established technique, well known in the art. Typically, whole blood is centrifuged with or without an isotonic buffer at low speed for a short period of time. Although the speed of centrifugation can vary, centrifugation at a range of about 600 to about 3900 rpm for about 5 to about 20 minutes at about $-10°-20°$ C. is usually sufficient to separate the RBCs from the other components. In one embodiment, for example, whole blood stored at 4° C. is centrifuged at 2000 rpm for about 20 minutes. The RBC concentrate is diluted 2-fold with a phosphate buffered saline. The blood fractionation step can occur before or after leukoreduction and/or the pathogen and white blood cell (WBC) inactivation and removal step.

Removal of WBCs from the pooled blood, leukoreduction, can be achieved by any known means of leukoreduction including, but not limited to, leukoreduction filters, gradient centrifugation, etc. (see, for example, LEUKOTRAP®, Pall Corp)

In another embodiment, the blood components are separated using a blood component separation system, such as the system described in co-pending U.S. patent application Ser. No. 13/291,822 filed on Nov. 8, 2011. Other blood component separation systems are known in the art and any system which produces a cell-containing product are suitable for use with the methods disclosed herein.

The separated blood components or whole blood units are pooled in a vat or container large enough to contain the blood components and any additional materials necessary (storage solution, additives, radiation sensitizers, photoquenchers, etc.). The vat or storage container maintains the blood components and additives in a sterile, temperature controlled environment and allows the addition or removal or material without exposure to a non-sterile environment.

Any number of units of whole blood, leukoreduced blood, RBCs, or platelets can be pooled. In certain embodiments, 5-100 units of whole blood or blood components are pooled. Alternatively, 10-100 units, 20-80, 30-70, 40-60, 5-10, 5-20, 5-30, 5-40, or 5-50 units of whole blood are pooled according to the methods disclosed herein.

The pooled blood components are then treated to inactivate any pathogens present in the donated blood. A variety of pathogens can be inactivated with the methods disclosed herein. In addition, residual WBCs not removed during leukoreduction, which can transmit pathogens contained within and also invoke immunogenic reactions, are removed and/or inactivated. Pathogen and WBC inactivation, in accordance with the methods disclosed herein, results in an eradication of pathogens while preserving the structure and function of the RBCs and platelets. In order to achieve Food and Drug Administration regulatory requirements, the post-transfusion 24 hour recovery of the RBCs must be greater than or equal to 75% following pathogen inactivation and subsequent storage, which is indicative of a high level of retention of intact cell function and structure. RBC viability can be assessed by visual inspection of the sample and/or by determining the percent hemolysis in a stored unit. RBCs suitable for transfusion must exhibit less than 1% hemolysis. Such analyses are routine in the art and can be conducted by the tetramethylbenzidiene (TMB) method or using a hematology analyzer (e.g., Beckman Coulter AcT). RBC viability and extent of the RBC storage lesion (i.e. membrane damage, ATP levels) impacts post-transfusion in vivo circulatory survival time. Methods for determining whether RBCs meet regulatory requirements are known to persons of ordinary skill in the art (see for example, Hess Jr for BEST collaborative, *Transfusion,* 2012 epub).

One or more methods of pathogen inactivation can be used in accordance with the disclosed methods. Via the inactivation procedures disclosed herein, pathogens in the whole blood or RBC component are reduced. Methods for determining infectivity levels are known to persons of ordinary skill in the art (see for example, *Thrombosis and Hemostasis,* 44:138-142, 1980). In accordance with the disclosed methods, at least $10^4$ infectious units of pathogen are inactivated. In certain embodiments, at least $10^5$ infection units or at least $10^6$ infectious units of pathogen are inactivated. Restated, inactivation of pathogen is obtained to the extent of at least "4 logs", and alternatively, greater than 5 logs or greater than 6 logs, such that pathogen in the sample is reduced to the extent determined by infectivity studies where that pathogen is present in the untreated sample in such a concentration that even after dilution to $10^4$, $10^5$, or $10^6$, pathogen activity can be measured. For the purposes of this disclosure, the terms "inactivate" and "reduce" both refer to a multiple log reduction in the number of viable pathogens in the whole blood or RBC component.

In certain embodiments, a pathogen in the blood cell product is inactivated using irradiation. The term "irradiation" refers to any form of radiation conventionally used to inactivate cells or pathogens (WBCs, viruses, parasites, bacteria, or other pathogenic organisms) either alone or in combination with some other agent or condition. Non-limiting examples of irradiation include ultraviolet (UVA, UVB, UVC), gamma-irradiation, X-irradiation, and visible light. Monochromatic light in the range of about 660-700 nm is included in this definition as well. Irradiation can be conducted in the presence of an agent that promotes inactivation or protects cells from the radiation. Exemplary agents are quenchers and radiation sensitizers (radiosensitizers).

In one embodiment, an effective amount of irradiation is applied in the presence of a mixture of (a) compound that quenches photodynamic type I reactions and a compound that quenches type II photodynamic reactions, and/or (b) a bifunctional compound that quenches both types of photodynamic reactions. A typical radiation fluence range is 5-100 $J/cm^2$ or 50-100 $J/cm^2$ for UVA, 0.02-2 $J/cm^2$ or 0.05-0.2 $J/cm^2$ for UVC, and 1-40 kGy for gamma-irradiation. Quenchers scavenge type I and or II reactions and thereby provide protection to the RBCs. Suitable quenchers are any known to react with both free radicals (type I quenchers) or reactive forms of oxygen (type II quenchers). Representative quenchers include unsaturated fatty acids, reduced sugars, cholesterol indole derivatives, azides (e.g., sodium azide), tryptophan, polyhydric alcohols (e.g., glycerol, mannitol), thiols (e.g., glutathione), superoxide dismutase, flavonoids (e.g., quercetin and rutin), amino acids, DABCO (1,4-diazabicyclo[2.2.2]octane), vitamins, and combinations thereof.

The irradiation process can be carried out over a temperature range of about 0°-42° C. In certain embodiments, the temperature is about 20°-27° C., or about 20°-25° C. The pathogen inactivation process is carried out for a time less than 24 hours, and in certain embodiments, less than 10, less than 8, or less than 4 hours. In certain embodiments, irradiation is carried out for about 1 minute to about 240 minutes or, alternately, about 5 minutes to about 120 minutes. During the inactivation process, the RBC suspension can be maintained at a pH range of about 6.5-8, preferably 7.2-7.6.

The irradiation process can occur in the presence of one or more radiation sensitizers. Suitable radiation sensitizers include, but are not limited to, phthalocyanines, purpurins, and other molecules resembling porphyrins, photoactive compounds excited by UV light (e.g., psoralen, 8-methoxypsoralen, 4'-aminomethyl-4,5',8-trimethylpsoralen, bergapten, angelicin), dyes that absorb light in the visible spectrum (e.g., pypericin, methylene blue, eosin, fluoresceins, flavins), dyes that absorb X-irradiation (e.g., brominated psoralen, brominated hematoporphyrin, iodinated phthalocyanine), and combinations thereof. The use of irradiation sensitizers is known in the art and is described in, for example, U.S. Pat. Nos. 5,120,649, 5,232,844, 6,136,586, and 6,548,242, the disclosures of which are incorporated herein by reference.

Following pathogen inactivation with agents, the agent can be removed, if necessary, by any known means such as, centrifugation, washing, dialysis, and/or adsorption onto hydrophobic matrices.

In lieu of, or in addition to, the above described pathogen inactivation methods, a solvent-detergent method can be used to inactivate pathogens in blood plasma. This method is described, for example, in U.S. Pat. No. 4,540,573, which is incorporated herein by reference. Organic solvents can be combined with anionic or nonionic detergents to kill pathogens. For instance, an organic solvent, such as tri(n-butyl) phosphate combined with nonionic detergents such as TWEEN 80 or TRITON X-100. Alternately, a nonanionic detergent, alcohol, ether, or mixtures thereof can be used. In one embodiment, plasma can be contacted with a dialkylphosphate or a trialkylphosphate having alkyl groups that contain 1 to 10 carbon atoms, preferably 2-10 carbon atoms. Mixture of such compounds can be used as well as phosphates having alkyl groups of different length chains, for example, ethyl di(n-butyl) phosphate. Mixtures of di- and trialkylphosphates can be utilized in accordance with the disclosure. Di- or trialkylphosphates can be used in an amount of about 0.01 mg/ml to about 100 mg/ml, preferably about 0.1 mg/ml to about 10 mg/ml. Treatment can occur at a temperature of about −5° to 70° C. In certain embodiments, treatment can occur at a temperature between about 0° and 60° C. Treatment can occur for about 1 hour to about 24 hours. Following pathogen inactivation of the RBC containing solution, the di-, trialkylphosphate, or nonionic detergent can be removed by any known means such as extraction (see U.S. Pat. No. 4,789,545), diafiltration with either insoluble (e.g., TEFLON microporous membranes), adsorption using chromatographic or affinity chromatographic supports, and/or precipitation.

Wetting agents can be used in conjunction with the di- and trialkylphosphates to enhance the contact of the pathogen with the di- and trialkylphosphates. In certain embodiments, the wetting agent is a nonionic detergent. Detergents containing polyoxyethylene derivatives of fatty acids, or partial esters of sorbitol anhydrides are suitable. Examples of such detergents include, but are not limited to commercially available products TWEEN 80, TWEEN 20, polysorbate 80, and nonionic oil soluble water detergents such as oxyethylated alkylphenol (aka TRITON X100). Zwitterionic detergents such as N-dodecyl-N,N-dimethyl-2-ammonio-1-ethane sulphonate and its congeners, or non-ionic detergents such as octyl-beta-D-glucopyranoside are also suitable. The amount of wetting agent can be in a range from about 0.001% to about 10%. In certain embodiments, the wetting agent is present in an amount of about 0.01% to about 1.5%.

Other known methods of pathogen inactivation such as heat treatment, pH manipulation, methylene treatment, additional radiation treatments (with or without a chemical agent, such as formaldehyde, cyanines, riboflavin), inactivation and removal with microparticles (see U.S. Pat. No. 6,730,230), magnetophoresis, microdevices utilizing immunomagnetic and microfluidic technology, and/or immunomagnetic beads, can be used.

As stated above, in certain embodiments of the disclosed methods, pathogens in the blood samples are vated. A number of blood-borne pathogens are known and, if present in a blood sample, can transmit disease to a recipient. Diseases such as human immunodeficiency virus (HIV), hepatitis, syphilis, malaria, babesiosis, brucellosis, leptospirosis, arboviral infection, relapsing fever, Creutzfeldt-Jakob disease, human T-lymphotropic virus type I, and viral hemorrhagic fever can be transmitted via blood. Accordingly, the categories of pathogens that can be inactivated using the disclosed methods include, but are not limited to, viruses (including cell-free lipid enveloped viruses, actively replicating cell-associated viruses, non-enveloped viruses, and latent cell-associated viruses), bacteria, fungi, prions, and parasites.

A number of viruses are blood borne and therefore transmittable via transfusion. Non-limiting examples of lipid-coated human viruses include, but are not limited to, vesicular stomatitis virus (VSV), moloney sarcoma virus, Sindvis virus, human immunodeficiency virus (HIV-1, HIV-2), human T-cell lymphotrophic virus-I (HTLV-I), hepatitis B virus, non-A, non-B hepatitis virus (NANB; aka hepatitis C), cytomegalovirus, Epstein Barr, virus, lactate dehydrogenase elevating virus, herpes group viruses, rhabdovirus, leukoviruses, myxoviruses, alphaviruses, arboviruses (group B), paramyxoviruses, arenaviruses, and coronaviruses.

Nonlimiting examples of non-enveloped virus that can be inactivated in accordance with the disclosed methods include parvovirus, polio virus, hepatitis A virus, enteric non-a, non-B hepatitis virus, bacteriophage M13, and satellite adeno-associated virus (AAV).

Bacterial contamination of blood products can cause infection in a recipient. Examples of bacterial infections that can be inactivated in accordance with the methods disclosed herein include *Yersinia pestis, Haemophilus influenzae, Staphylococcus aureus, Neisseria meningitides, Neisseria gonorrhoeae*, and *Streptococcus pyogenes*.

Protozoa can cause a number of infections in humans, including, but not limited to, malaria, amoebiasis, babesiosis, giardiasis, toxoplasmosis, cryptosporidiosis, trichomoniasis, leishmaniasis, trypanosomiasis, and sleeping sickness. The organisms causing these illnesses can be inactivated in accordance with the disclosed methods.

Some fungi can cause disease in humans, including, but not limited to, aspergilloses, candidoses, coccidioidomycosis, cryptococcosis, histoplasmosis, mycetomas, and paracoccidioidomycosis. The fungi leading to these and other infections can be inactivated with the disclosed methods.

Prions are proteinaceous infection particles that cause a number of diseases in mammals. In humans, prions are associated with Creutzfeldt-Jakob disease (i.e., mad cow disease). Prion inactivation or removal may be achieved with the pathogen inactivation methods disclosed herein or by other methods known to persons of ordinary skill in the art, such as filtration.

In additional embodiments, pooled units of whole blood having the same blood type and/or blood group are passed through a leukoreduction filter and the leukoreduced RBC-containing component is collected. The leukoreduced RBC-containing component includes RBCs, platelets and plasma is then pathogen inactivated, and the inactivation agent is removed, inactivated, or otherwise rendered harmless. The leukoreduced, pathogen inactivated RBC-containing component is then separated into components such as RBCs, platelets, and/or plasma according to the disclosure in co-pending U.S. patent application Ser. No. 13/291,822 filed on Nov. 8, 2011 and incorporated by reference herein, and each component is transferred into a storage container. Platelets and RBCs are transferred into storage containers with an appropriate storage solution. Each component is then divided into uniform units of suitable dose and volume for transfusion and stored under the appropriate conditions. Only as an example, RBCs are optimally stored at 1-6° C., plasma is stored at −18° C. or below, and platelets are stored at 20-24° C. The method optionally comprises filtering to remove poorly-deformable RBCs from any RBC-containing preparation.

In yet another embodiment, pooled units of whole blood having the same blood type and/or blood group are collected into a container suitable for centrifugation or similar separation method, such as the method of co-pending U.S. patent application Ser. No. 13/291,822 filed on Nov. 8, 2011 incorporated by reference herein. The pooled whole blood is then centrifuged or separated into a plasma fraction and a cellular fraction containing red blood cells, white blood cells and platelets. The plasma fraction is collected and subjected to solvent/detergent pathogen inactivation and the pathogen-inactivated plasma is processed into uniform volume units and stored at −18° C. or below. The cellular fraction is leukoreduced and the leukoreduced fraction (red blood cells and platelets) is pathogen inactivated and following inactivation the inactivation agent is removed, inactivated, or otherwise rendered harmless. The pathogen-inactivated cellular fractions is separated into red blood cells and platelets by filtration or centrifugation, including methods disclosed in co-pending U.S. patent application Ser. No. 13/291,822 filed on Nov. 8, 2011 incorporated by reference herein. Platelets are collected in a platelet storage solution and separated into units of uniform volume and dose and stored at 20-24° C. RBCs are collected in a preservation solution and distributed into units of uniform volume and dose and stored at 1-6° C. The method optionally comprises filtering to remove poorly-deformable RBCs from any RBC-containing preparation.

In one embodiment, red blood cell pools are filtered prior to storage to remove poorly-deformable red blood cells in an artificial spleen filtering system. The filtering system can comprise any filtering material having pores (or channels) in the range of 1 to 10 μm such that rigid red blood cells are retained by the filter system and deformable (normal) red blood cells pass through the filter system. In this manner, poorly-deformable red blood cells in a red blood cell preparation are removed prior to, or after, storage to prevent certain transfusion-related adverse effects in the transfusion recipient.

In certain embodiments, the pores (or channels) of the filtering unit have a diameter in the range of 1 to 10 μm, in the range of 1.85 to 9.4 μm, or 1 to 3, or 1 to 2 μm, for example a diameter of 2 μm. In another embodiment, the channels of the filtering unit have a thickness of less than 24 μm, and preferably less than 5 μm.

The flow of red blood cells through the filtering unit is driven by gravity, flush (for example by applying a constant pressure), aspiration, or by centrifugation. In one embodiment, the filtering unit is placed in a column (for example when the flow through the filtering unit is driven by gravity or flush) or in a tube (for example when the flow through the filtering unit is driven by centrifugation).

In one embodiment, the filtering unit comprises or consists of channel-perforated membrane(s), for example polycarbonate channel-perforated membrane(s). Channel-perforated membranes from Sterlitech Corporation in which channel diameter is in the range of 1 to 3 μm and channel length is 24 μm are particularly appropriate. For example, 2 μm-wide and 24 μm-thick polycarbonate channel-perforated membranes from Sterlitech Corporation can be used.

When channel-perforated membrane(s) are used, the flow through the filtering unit is generally gravity-driven. In particular, flow can be gravity driven and performed under a constant pressure, for example a constant pressure of 80-85 cm of water, and preferably at a temperature of about 34-37° C.

Alternatively, the filtering unit can comprise or consist of one or several layer(s) of beads, wherein beads present in the filtering unit have a diameter in the range of 2-25 μm or 5-25 μm, and wherein channels (pores) formed by the inter-bead space within the filtering unit preferably varies between 0.74 and 9.4 µm or 1.85 µm and 9.4 µm. Suitable beads include, but are not limited to tin beads, polymeric beads, glass bead, or any other beads capable of forming pores of the desired size.

In one embodiment, each layer of beads present in the filtering unit is at least 0.5-10 µm thick, the total thickness of beads in the filtering unit being of at least 5 mm, preferably 7 mm. For example, a layer of a thickness of at least 5 mm and preferably 7 mm, composed of a mixture of equal weight of beads the diameter of which is ranging from 5 to 15 µm and beads the diameter of which is ranging from 15 to 25 µm can be used. In another embodiment, a 7 mm-thick layer of beads the diameter of which is ranging from 5 to 25 µm is used. In another embodiment, the filtering unit comprises a 7 mm-thick layer of beads the diameter of which is ranging from 5 to 25 µm and a layer above comprising beads of lower diameter than 5 µm. In the filtering unit, the layers of beads are staked up on a filter suitable to maintain the beads and that is not involved in the retention capacity of the filtering unit.

When layer(s) of beads are used, the flow through the filtering unit is generally obtained using a syringe-pressured flow or by centrifugation (for example by centrifuging at 1500-2500 g). For example, an electric pump can be used to generate a constant flow of suspending medium (for example PBS+1% Albumax II) through the layer. The upper pressure limit can be for example 999 mbars. Alternatively, the flow through the filtering unit can also be obtained using other techniques, and can, for example, be gravity-driven.

In another embodiment, layer(s) of beads are used and step a) is performed under a constant pressure, for example a constant pressure of 80-85 cm of water, and preferably at a temperature of about 20-25° C.

Before or after addition of a storage solution, a plurality of platelet or RBC units are prepared in which each unit has an approximately uniform dose of RBCs or platelets. The pooled platelets or RBCs are kept suspended in solution by any known means (mechanical agitation, fluid agitation) in order to maintain the platelets or RBCs evenly distributed in solution such that a unit having a uniform dose of platelets or RBCs can be prepared. By uniform dose, it is meant that the amount of platelets or RBCs, i.e., the number of platelets or RBCs per unit, does not vary by more than about 20%, about 15%, about 10% or about 5% from unit to unit. The size of a unit prepared in accordance with the disclosed methods can vary depending on the desired use. That is, the platelets or RBCs can be stored in smaller and/or larger aliquots in order to serve neonatal, pediatric and/or adult populations. In general, RBC units contain at least about $1 \times 10^9$ RBCs/mL, at least about $5 \times 10^9$ RBCs/mL, or at least $1 \times 10^{10}$ RBCs/mL. Alternatively, the uniform dose of RBCs is $1-5 \times 10^{12}$ RBCs per unit. In additional embodiments, the uniform dose of RBCs is $2-4 \times 10^{12}$ RBCs per unit or $2-3 \times 10^{12}$ RBCs per unit.

Additionally, a "uniform dose of RBCs" can refer to a uniform concentration of RBCs in each unit which will allow for a standardized range of hemoglobin concentration per unit of RBCs independent of the RBC concentration of the donor blood. In one embodiment, each unit contains 20-80 grams of hemoglobin, 30-70 grams of hemoglobin, 40-60 grams of hemoglobin, or about 50 grams of hemoglobin per unit of RBCs In general, the uniform dose of platelets is $1-6 \times 10^{11}$ platelets per unit. In additional embodiments, the uniform dose of platelets is can be $2-6 \times 10^{11}$ platelets per unit, $2-4 \times 10^{11}$ platelets per unit, $2-3 \times 10^{11}$ platelets per unit, $3-4 \times 10^{12}$ platelets per unit, or $3-5 \times 10^{11}$ platelets per unit. Following pathogen inactivation, platelets and RBCs are stored in a storage solution. The RBC storage solution can be any that preserves 2,3-diphosphoglycerate (DPG) and maintains high adenine triphosphate (ATP) concentrations, minimizes hemolysis (hemolysis <1%), and reduces potassium leak, thereby improving the structure and function of the stored RBCs. RBC storage solutions are known in the art (e.g., ADSOL, Baxter Healthcare, Deerfield, IL; SAGM [saline-adenine-glucose-mannitol] and PAGGSM [phosphate, adenine, glucose, guanosine, saline and mannitol]). The storage solutions disclosed herein include one or more of adenine, glucose, sodium phosphate, mannitol, dextrose, sodium chloride, sodium citrate, citric acid, and guanosine. In one embodiment, the storage solution comprises adenine, glucose, sodium phosphate, mannitol and guanosine. In an alternative embodiment, the platelet storage solution is a platelet additive solution such as, but not limited to, InterSol™ (Fenwal Inc.), examples of which are know to persons of ordinary skill in the art.

RBCs, using known protocols and storage solutions, can be stored for approximately 42 days before administration to a subject, after which time the structure, function and viability of the of the RBCs is compromised. In contrast, using the disclosed methods, the obtained RBC product can be stored for about 42 days to about 100 days, or for about 60 days to about 100 days, or for about 70 days to about 90 days. The units can be stored at a temperature of about 1°-6° C. Further, in accordance with the disclosed methods, the biochemical changes (loss of 2,3-DPG/ATP, inability to release adequate oxygen, potassium leakage), biomechanical changes (deformation of biconcave disc, impaired movement through microcirculation, hemolysis), and immunologic changes that occur in ex vivo storage of RBCs (collectively referred to as "RBC storage lesion") are reduced. These changes can greatly affect RBC and patient survival post-transfusion and therefore, a reduction in one or more of these parameters can confer significant advantages and increase the success of the RBC transfusion.

In an additional embodiment, RBC units are filtered post-storage, just prior to transfusion, to remove poorly-deformable RBCs.

The methods disclosed herein can be performed utilizing known equipment and reagents. Any available assortment of collection tubing, collection bags, and storage bags or other types of vessels can be used in accordance with the disclosed methods. In certain embodiments, di(2-ethylhexyl) phthalate (DEHP) free tubing, collection, and storage bags are desirable.

The methods disclosed herein are well suited for a variety of settings, including but not limited to, community and other blood banks, military sites, hospitals, and clinics.

EXAMPLE 1

Approximately 5 to 100 units of whole blood of the same type and group and leukoreduced and pooled. The pooled leukoreduced blood (RBCs, plasma, and platelets) is treated with UV radiation and optionally a type I and II quencher and/or radiation sensitizer to remove any pathogen and vate residual WBCs. If a quencher or radiation sensitizer is present, the cells are washed prior to continuing. The material is then fractionated into plasma, RBCs and platelets. A storage solution of adenine, glucose, sodium phosphate, mannitol and guanosine is added to the RBC component following pathogen inactivation. A filtering step is optionally added to remove poorly-deformable RBCs from any RBC-containing component. The resultant RBC-containing composition is further divided into RBC units comprising a uniform number and volume of RBCs/mL. The units are stored at 1°-6° C.

A storage solution is added to the platelet component following pathogen inactivation and the resultant platelet-containing composition is further divided into platelet units comprising a uniform number and volume of platelets/mL. The units are stored at 20°-24° C.

The plasma component is further divided into plasma units comprising a uniform volume of plasma. The units are stored at −18° C. or below.

EXAMPLE 2

The cell containing composition from Example 1 is analyzed for stability and viability of RBCs at a time period of 20 days, 40 days, 60 days and 100 days. Analysis of ATP and 2,3-DPG levels and percentage hemolysis as well as post-transfusion survival studies are used to determine the stability and viability of the RBCs in the cell containing solution. Storage life of the cell containing composition is determined therefrom.

EXAMPLE 3

About 100 units of blood are same blood group and type are individually subjected to a process of leukoreduction with a leukoreduction filter and subsequently fractionated via centrifugation for about 20 min at 2000 rpm. The isolated RBCs from each unit are washed with a phosphate buffered saline are and then pooled. The pooled RBCs are further subjected to UV radiation for about 2-4 hours or to inactivate any pathogenic contaminants. A storage solution is added to the RBCs and the RBCs are gently agitated by mechanical means to maintain the RBCs uniformly dispersed in the storage solution. The RBCs are divided into units having a uniform number of RBCs/m L. The units are stored at 1°-6° C. for about 42 to about 100 days prior to use.

EXAMPLE 4

Figure 2:
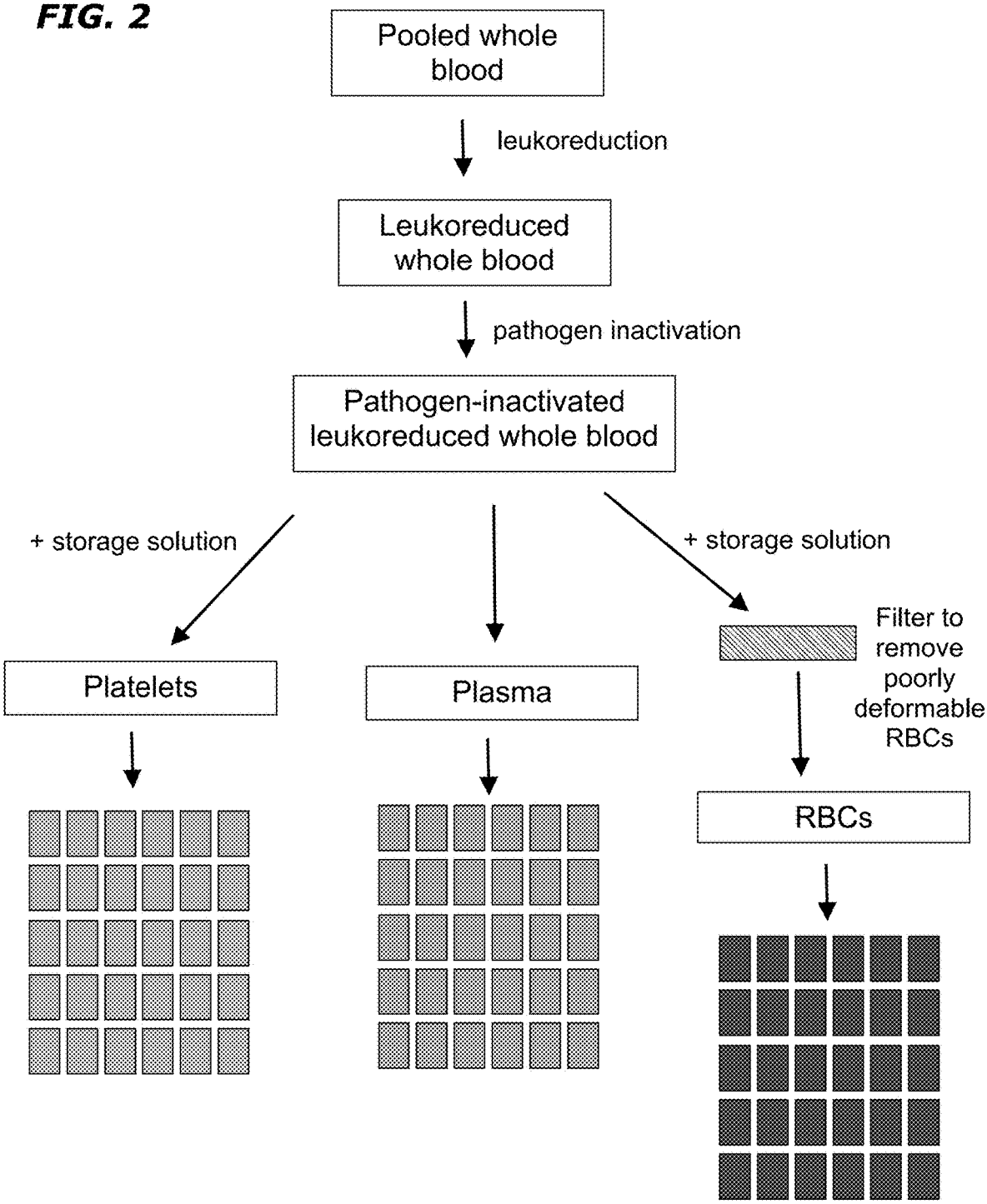
FIG. 2 depicts a scheme for producing uniform doses of plasma, platelets, and RBCs in which whole blood is pooled and leukoreduced prior to fractionation into plasma, platelets and RBCs. The scheme optionally includes a filter to remove poorly-deformable RBCs from an RBC component.

Approximately 5 to 100 units of whole blood of the same type and group (i.e., ABO, Rh, etc.) are collected and leukoreduced as depicted in FIG. 2. The leukoreduced blood is treated via UV radiation and a type I and II quencher to remove any pathogens and inactivate residual WBCs. Platelets, RBCs, and plasma are then separated in one step or in multiple steps. A storage solution of adenine, glucose, sodium phosphate, mannitol and guanosine is added to the RBCs following pathogen inactivation. The method optionally comprises the addition of a filter to remove poorly-deformable RBCs from any RBC-containing preparation. The resultant RBCs are aliquoted into units comprising a uniform volume and number of RBCs/mL. The units are stored at 1°-6° C. A storage solution is added to the separated platelets and the platelets are aliquoted into units comprising a uniform volume and number of platelets/mL and stored at 20-24° C. The plasma fraction is aliquoted into uniform volume units and stored at −18° C. or below.

EXAMPLE 5

Figure 3:
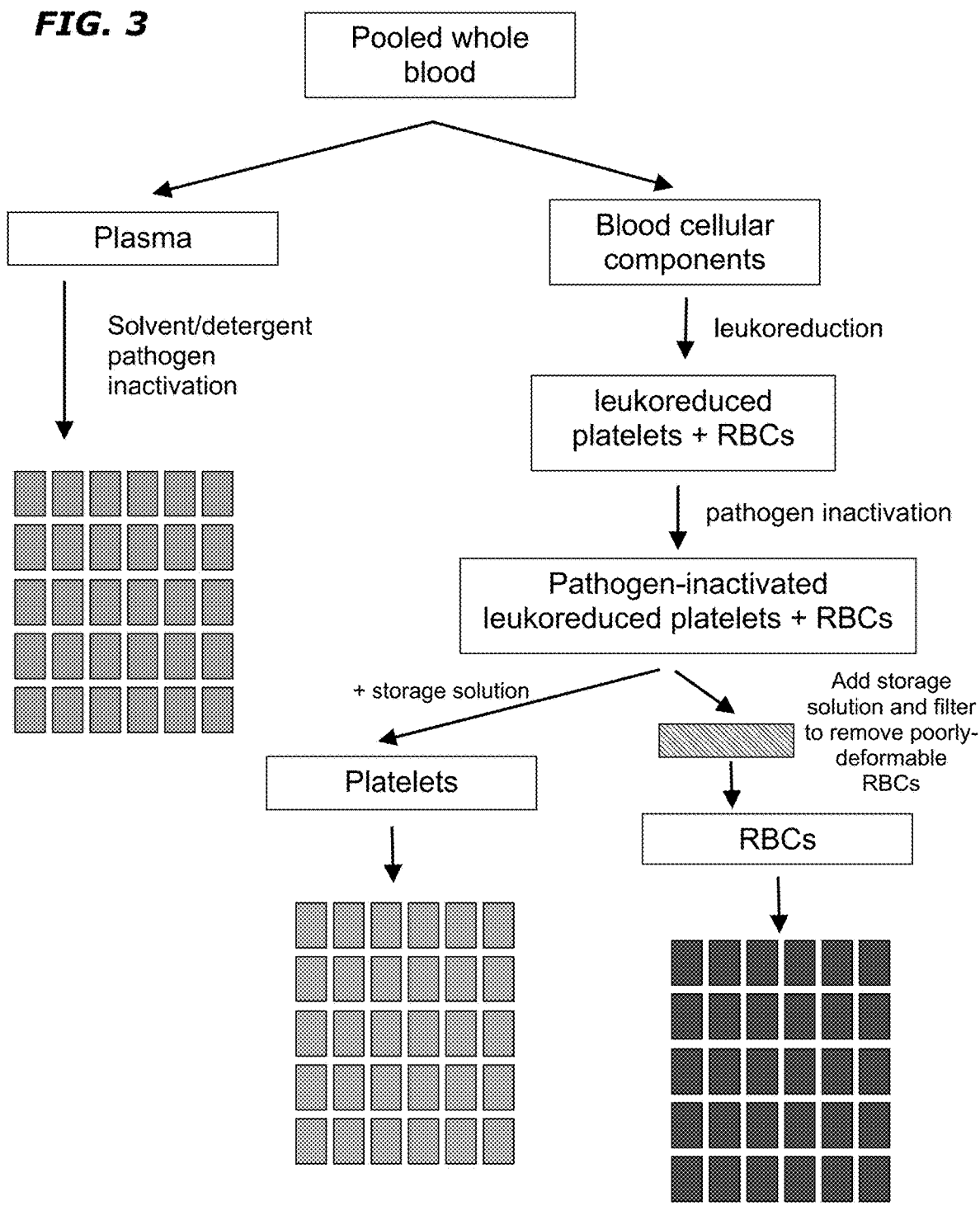
FIG. 3 depicts a scheme for producing uniform doses of plasma, platelets, and RBCs in which the whole blood is fractionated into plasma and cellular fractions and the cellular fraction is further leukoreduced and fractionated into platelets and RBCs. The scheme optionally includes a filter to remove poorly-deformable RBCs from an RBC component.

Approximately 5 to 100 units of whole blood of the same type and group (i.e., ABO, Rh, etc.) are collected and separated into plasma and cellular fractions as depicted in FIG. 3. The plasma fraction is treated with solvent/detergent to inactivate viruses and then aliquoted into uniform volume units and stored at −18° C. or below. The cellular fraction is leukoreduced and is treated via UV radiation and a type I and II quencher to remove any pathogens and inactivate residual WBCs before separating into platelets and RBCs. A storage solution of adenine, glucose, sodium phosphate, mannitol and guanosine is added to the RBCs following pathogen inactivation. The method optionally comprises the addition of a filter to remove poorly-deformable RBCs from any RBC-containing preparation. The resultant RBCs are aliquoted into units comprising a uniform volume and number of RBCs/mL. The units are stored at 1°-6° C. A storage solution is added to the separated platelets and the platelets are aliquoted into units comprising a uniform volume and number of platelets/mL and stored at 20-24° C.

EXAMPLE 6

Filtration of poorly-deformable RBCs is conducted before or after storage of pooled or single-unit leukocyte-reduced RBCs.

Filtration with Channel-Perforated Membranes

Column surfaces and membranes are blocked with suspending medium (RPMI+4% albumin+5% Plasmion®) during 15 minutes prior to introduction of RBCs. RBCs are allowed to flow through 24 μm-thick polycarbonate membranes perforated with 0.8-8 μm-wide channels (Sterlitech Corporation), after suspension at 2%-2.5% hematocrit in RPMI supplemented with 4% albumin and 5% Plasmion®. Filtration is performed at 34-37° C. under a constant pressure (80-85 cm of water). Flow is typically unimpaired when the channel diameter was 3 μm whereas no flow is observed through pores the diameter values of which are 1 μm. No retention of poorly-deformable RBCs is observed when channel width is 3 μm.

"Upstream" and "downstream" RBC sub-populations can be retrieved and centrifuged (2 minutes at 1500 g) and the obtained RBC pellets used for quantification or analysis.

Bead Filtration

RBCs are allowed to flow through 0.5-2 mm-thick layers of beads (such as, for example, tin beads from Industrie des poudres spheriques (IPS), Annemasse, France) of increasing diameter (from 2-12 μm, 5-15 μm, 15-25 μm and more than 40 μm) after suspension at 2-2.5% hematocrit in PBS or RPMI supplemented with 1% albumax II® (Gibco). Filtration is performed at 20-25° C. under a constant pressure (80-85 cm of water). Column surfaces and bead layers are blocked with suspending medium (PBS+1% Albumax II®) during 15 minutes prior to introduction of RBCs. Retention of RBCs with thin bead layers made of beads of diameter 5-15 or 15-25 or more than 40 μm, or with only the filter in the tip used to maintain the bead layers. A mixture of equal weight of 5-15 μm and 15-25 μm (thereafter referred to as "5-25 μm layer") induces the retention of RBCs provided that the thickness of the layer is >5 mm.

An electric pump is used to generate a constant flow of solution through the layer. Upper pressure limit is 999 mbars.

Centrifugation-based filtration. Alternatively, bead-containing tips are used as filtering units then centrifuged at 1500-2500 (until the whole sample has flown through). The bead layer(s) are rinsed of suspending medium by the same centrifugation method. Upstream, downstream and retained RBC sub-populations can be retrieved and processed for quantification as described below.

The "upstream" sample can be reserved prior to filtration, centrifuged (1500 g), and the obtained RBC pellet can be used for quantification. The "downstream" sample containing RBCs that had flown through the bead layer can be centrifuged at 1500 g, and the thus obtained RBC pellet used for quantification.

The bead layer is retrieved at the end of the filtration process. Three steps of decantation by gravity allows for the retrieval of an RBC pellet containing minimal beads.

Filtration is associated with a significant retention of poorly-deformable RBCs.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for preparing uniform dose blood component transfusion products from a plurality of whole blood units of a same blood group and type comprising:
    a) pooling a plurality of units of whole blood from different donors of the same blood group and type;
    b) leukoreducing the pooled whole blood;
    c) treating the pooled whole blood to inactivate one or more pathogens;
    wherein the leukoreduction and inactivation steps are performed in either order;
    d) separating at least one of an RBC component, a platelet component, and a plasma component from the leukoreduced, pathogen-inactivated pooled whole blood;
    and performing at least one of steps e), f), or g):
    e) adding a storage solution to the RBC component and dividing the RBC component into uniform volume and dose RBC transfusion product units;
    f) adding a storage solution to the platelet component and dividing the platelet component into uniform volume and dose platelet transfusion product units; and
    g) dividing the plasma component into uniform volume and dose plasma transfusion product units.

2. The method of claim 1, wherein the storage solution comprises at least one material selected from the group consisting of adenine, glucose, phosphate, mannitol, guanosine, and a combination thereof.

3. The method of claim 1, wherein the treating step inactivates one or more pathogens without damaging the structure or function of a cell component.

4. The method of claim 1, wherein the one or more pathogens are selected from the group consisting of viruses, bacteria, fungi, prions, parasites, and combinations thereof.

5. The method of claim 1, wherein the one or more pathogens are inactivated by at least one method selected from the group consisting of irradiation, solvent and detergent, magnetophoresis, immunomagnetic bead technology, filtration, and a combination thereof.

6. The method of claim 1, wherein each unit of the RBC component contains about $1 \times 10^{12}$ to about $5 \times 10^{12}$ RBCs/unit.

7. The method of claim 1, wherein each unit of the RBC component contains about 20-80 g of hemoglobin/unit.

8. The method of claim 1, wherein each unit of the platelet component contains about $2-6 \times 10^{11}$ platelets/unit.

9. The method of claim 1, further comprising the step of filtering out poorly-deformable RBCs from an RBC or blood component.

10. The method of claim 1, wherein the leukoreduction step is performed prior to the pathogen inactivation step.

11. The method of claim 1, wherein the pathogen inactivation step is performed prior to the leukoreduction step.

12. The method of claim 1, wherein any two of steps e), f), or g) are performed.

13. The method of claim 1, wherein all three of steps e), f), and g) are performed.

14. The method of claim 1, further comprising inactivating residual white blood cells in the RBC component of step d).

15. The method of claim 1, wherein the blood group and type is selected from ABO, Rh, and a combination thereof.

* * * * *